(12) United States Patent
Ayre

(10) Patent No.: US 7,988,728 B2
(45) Date of Patent: Aug. 2, 2011

(54) PHYSIOLOGICAL DEMAND RESPONSIVE CONTROL SYSTEM

(75) Inventor: Peter Joseph Ayre, Crows Nest (AU)

(73) Assignee: Thoratec Corporation, Pleasanton, CA (US)

( * ) Notice: Subject to any disclaimer, the term of this patent is extended or adjusted under 35 U.S.C. 154(b) by 1090 days.

(21) Appl. No.: 10/529,657

(22) PCT Filed: Sep. 30, 2003

(86) PCT No.: PCT/AU03/01281
§ 371 (c)(1),
(2), (4) Date: Nov. 28, 2006

(87) PCT Pub. No.: WO2004/028593
PCT Pub. Date: Apr. 8, 2004

(65) Prior Publication Data
US 2008/0183287 A1 Jul. 31, 2008

(30) Foreign Application Priority Data
Sep. 30, 2002 (AU) ................................ 2002951685

(51) Int. Cl.
*A61M 1/10* (2006.01)
(52) U.S. Cl. ...... 623/3.28; 623/3.1; 623/3.13; 623/3.14; 623/3.15; 623/3.24; 623/3.25; 604/66; 604/67; 600/16; 600/17; 73/54.28; 73/54.38
(58) Field of Classification Search ............. 623/3.1, 623/3.13, 3.14, 3.15, 3.24, 3.25, 3.28; 604/66–67; 600/16–17; 73/54.28, 54.38
See application file for complete search history.

(56) References Cited

U.S. PATENT DOCUMENTS

| | | | |
|---|---|---|---|
| 5,289,821 A | 3/1994 | Swartz | |
| 5,888,242 A | 3/1999 | Antaki et al. | |
| 6,027,498 A | 2/2000 | Mutch et al. | |
| 6,066,086 A * | 5/2000 | Antaki et al. | 600/17 |
| 6,068,588 A * | 5/2000 | Goldowsky | 600/16 |
| 6,071,093 A | 6/2000 | Hart | |

(Continued)

FOREIGN PATENT DOCUMENTS

EP 1 354 606 10/2003

(Continued)

OTHER PUBLICATIONS

Maeda, K. et al.; Asaio Transactions, "Predictive control by physical activity rate of a total artificial heart during exercise;" vol. 34, No. 3, Jul. 1988, pp. 480-484.

(Continued)

*Primary Examiner* — Carl H Layno
*Assistant Examiner* — Deborah Malamud
(74) *Attorney, Agent, or Firm* — Squire, Sanders & Dempsey (US) LLP

(57) ABSTRACT

A demand responsive physiological control system for use with a rotary blood pump; said system including a pump controller which is capable of controlling pump speed of said pump; said system further including a physiological controller, and wherein said physiological controller is adapted to analyse input data relating to physiological condition of a user of said pump; and wherein said physiological controller determines appropriate pumping speed and sends a speed control signal to said pump controller to adjust pump speed; said system further including a physiological state detector which provides said input data indicative of at least one physiological state of said user, in use, to said physiological controller.

22 Claims, 9 Drawing Sheets

U.S. PATENT DOCUMENTS

| | | | |
|---|---|---|---|
| 6,277,078 | B1 | 8/2001 | Porat et al. |
| 6,623,420 | B2 | 9/2003 | Reich et al. |
| 6,991,595 | B2 | 1/2006 | Burke et al. |
| 7,138,776 | B1 | 11/2006 | Gauthier et al. |
| 7,494,459 | B2 * | 2/2009 | Anstadt et al. ............ 600/17 |
| 7,645,225 | B2 | 1/2010 | Medvedev et al. |
| 2001/0009645 | A1 | 7/2001 | Noda |
| 2002/0183628 | A1 | 12/2002 | Reich et al. |

FOREIGN PATENT DOCUMENTS

| | | |
|---|---|---|
| WO | WO 01/05023 | 1/2001 |
| WO | WO 01/72352 | 10/2001 |

OTHER PUBLICATIONS

International Search Report, dated Feb. 9, 2004.

Maeda, K. et al.; Asaio Transactions, "Predictive control by physical activity rate of a total artificial heart during exercise;" vol. 34, No. 3, Jul. 1988, pp. 480-484.

Maeda, K. et al.; Asaio Transactions, "Predictive control by physical activity rate of a total artificial heart during exercise;" vol. 34, No. 3, Jul. 1988, Abstract.

* cited by examiner

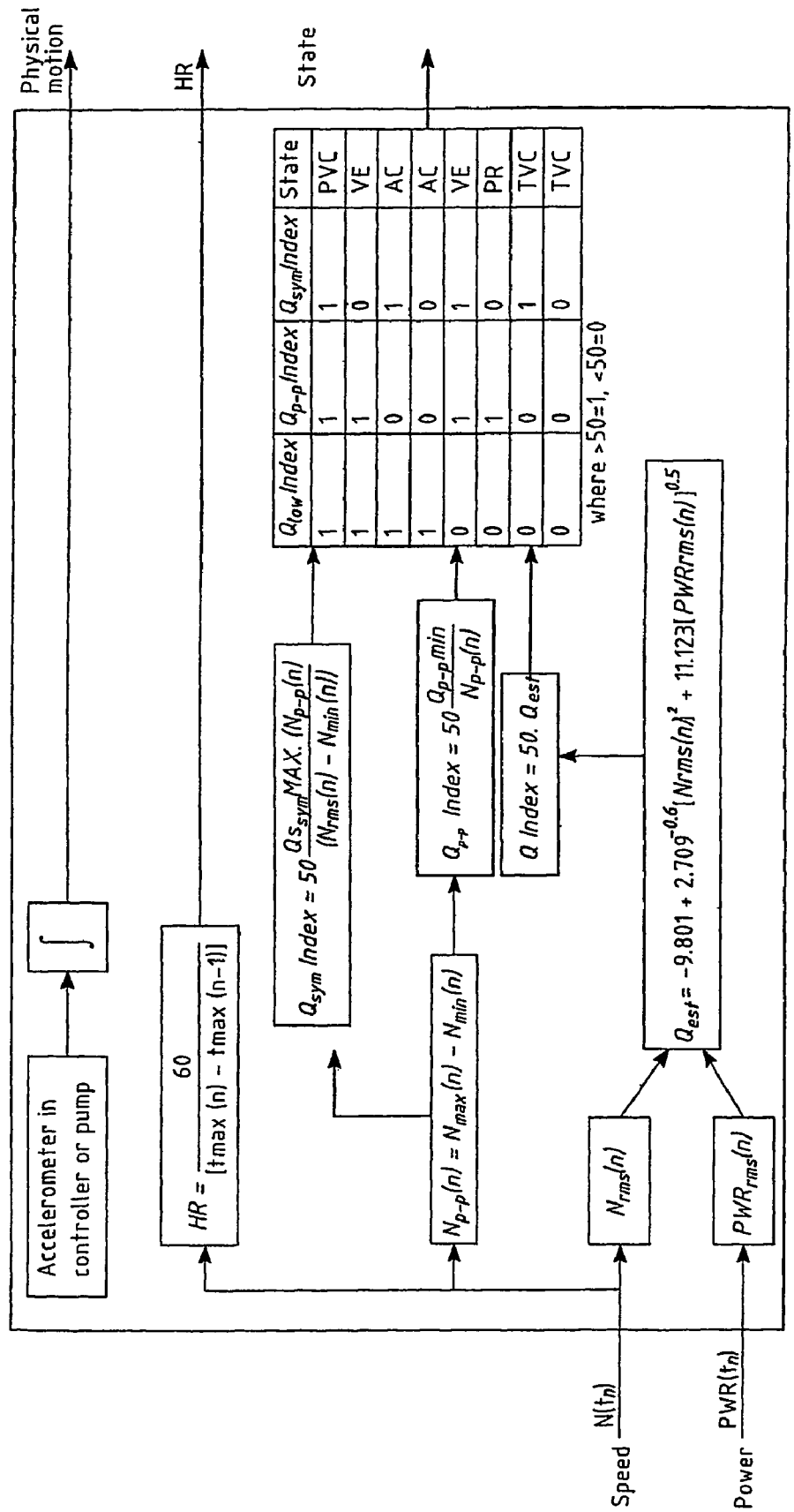

Fig. 6

A block diagram of the Pumping state detection module. From Instantaneous pump speed and power ($N(t)$, $PWR(t)$), rms speed and RMS power ($N_{rms}(n)$, $PWR_{rms}(n)$) were derived. From the RMS parameters, pump flow, $Q_{estRMS}(t)$) was derived. Pumping state indexes for TVC, PVC AC, VE, PR were generated from the RMS and instantaneous speed parameters given flow rate boundaries. Heart rate derived from $N(t)$ and physical motion intergrating the output of an accelerometer mounted in the controller or pump.

Flow chart for determining pump drive set point change through the integration of the 3 methods of non-invasive detection (physical motion, HR and state detection) for exercise rate response control.

HQ curves for the pump and a typical centrigugal pump which exhibits a peak in the HQ curve.

PHYSIOLOGICAL DEMAND RESPONSIVE CONTROL SYSTEM

The present invention relates to a demand responsive physiological control system and, more particularly, to such a system particularly suited for use with blood pumps and, even more particularly, those used to assist heart function such as, for example, ventricular assist devices.

BACKGROUND

With particular reference to physiological control systems in mammals and more particularly those of the human body it has been noted that the control systems which the body itself uses to control various organs are complex.

For example, the heart of a mammal may cause the amount of blood that is to be circulated through the body to change not just for what might be termed obvious reasons such as an increase in physical exertion by a person, but may also occur for example, as a result of anticipation of exertion. Furthermore the triggers which can cause changes in heart rate and pumped blood volume may derive from the nervous system directly or may derive from the action of hormones or other chemical releases within the body.

It follows, where mechanical aids are introduced into the body to assist the body's functions such as, for example, implantable rotary blood pumps used as ventricular assist devices that simplistic control mechanisms for these mechanical aids cannot hope to anticipate or mimic the commands which the body may pass to the heart.

For example, in early applications of ventricular assist devices the control mechanisms simply set the ventricular assist device to pump at a constant volume per unit time, adjusted at the time of initial installation to best suit the patient in whom the device has been installed.

Such systems use pump speed as the controlled variable. Unfortunately, a set pump speed bears no relation to actual physiological demand.

It is an object of the present invention to address or ameliorate one or more of the above mentioned disadvantages.

BRIEF DESCRIPTION OF INVENTION

Accordingly, in one broad form of the invention there is provided a demand responsive physiological control system for use with a rotary blood pump; said system including a pump controller which is capable of controlling pump speed of said pump; said system further including a physiological controller, and wherein said physiological controller is adapted to analyse input data relating to physiological condition of a user of said pump; and wherein said physiological controller determines appropriate pumping speed and sends a speed control signal to said pump controller to adjacent adjust pump speed; said system further including a physiological state detector which provides said input data indicative of at least one physiological state of said user, in use, to said physiological controller.

Preferably said the physiological state detector includes an accelerometer to sense motion of the user, when in use.

Preferably said the accelerometer senses motion in at least one axis.

Preferably said the accelerometer senses motion in three orthogonal axes.

Preferably said system includes a pump monitor that detects information relating to voltage and current of the pump and delivers this information to said physiological controller.

Preferably said pump monitor detects an instantaneous pump impeller speed of the rotary blood pump through measurements.

Preferably said pump monitor detects non-invasively.

Preferably said physiological controller uses said information received from the pump monitor to derive mathematically an appropriate pump speed.

Preferably said physiological controller assesses flow dynamics and an average flow estimate, developed from speed and input power supplied to the pump by the pump controller.

Preferably said physiological controller mathematically determines a pumping state and if a deleterious state is determined the speed control signal is changed accordingly.

In a further broad form of the invention there is provided a physiological detector includes a means of detecting and quantifying a heart rate of the user, when in use.

Preferably said physiological detector includes a means of non-invasively detecting and quantifying a heart rate of the user, in use.

Preferably said physiological controller can determine a heart rate of the user by sensing speed of the pump.

Preferably said physiological controller can determine a heart rate of the user using power inputted to the pump.

Preferably said pump is internally implantable within the user.

Preferably said the pump is a ventricle assist device.

Preferably said the pump has a hydrodynamic bearing that produces a relatively flat pump head versus pump flow curve.

Preferably said physiological controller is capable of manual manipulation by the user.

Preferably said manual manipulation is within adjustable predefined limits.

Preferably said physiological controller is adapted for communication with a computer and wherein the physiological controller is adapted for manipulation by a software user interface.

Preferably said physiological controller includes an alarm.

In a further broad form of the invention there is provided a process for using physiological demand data to optimize pump speed of a rotary blood pump wherein the process comprises of the following steps: a heart rate of the user is non-invasively determined; a level of physiological exertion of the user is determined through non invasive means; an instantaneous pump speed and input power is used to calculate instantaneous blood flow rate; a pumping state is mathematically determined; the heart rate, pumping state and level of physical exertion are compared to the blood flow rate; and the pumping speed of the rotary blood pump is changed to appropriately supply the user with the correct blood flow rate.

In yet a further broad form of the invention there is provided a pump control system for a pump for use in a heart assist device; said system comprising data processing means which receives body motion information and heart rate information thereby to derive a speed control signal for impeller speed of an impeller of said pump.

Preferably said body motion information is derived from an accelerometer.

Preferably said accelerometer senses motion in a single axis.

Preferably said accelerometer senses motion in three orthogonal axes.

Preferably said heart rate information is derived from a non-invasive sensor.

Preferably said heart rate information is derived from voltage and current applied to an electric motor driving said impeller.

In yet a further broad form of the invention there is provided a method of control of pump speed of a blood pump; said method comprising establishing a base set point speed; said method further comprising establishing one or more criteria which, if satisfied, cause establishment of at least a second set point speed; said second set point speed higher than that of said base set point speed.

BRIEF DESCRIPTION OF DRAWINGS

Embodiments of the present invention will now be described with reference to the accompanying drawings wherein:

FIG. 6 is a block diagram of a pumping state detection module for use with the second embodiment;

DETAILED DESCRIPTION OF PREFERRED EMBODIMENTS

Figure 1:
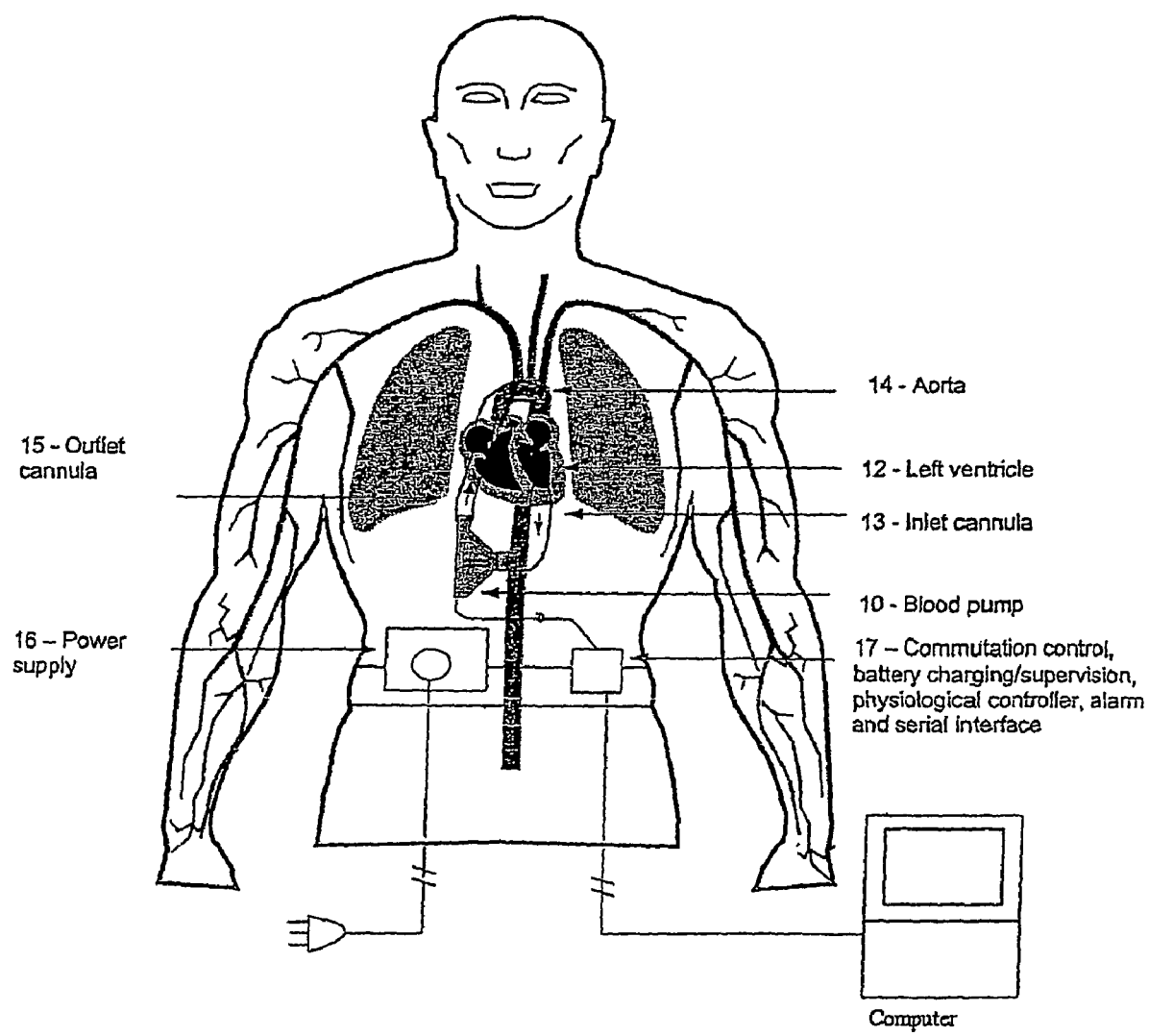
FIG. 1 is a diagram of a ventricular assist device installation within a human body suitable for control by embodiments of the present invention.

With initial reference to FIG. 1 there is illustrated in diagrammatic form a blood pump 10 installed within a human body 11 and arranged to function as a left ventricular assist device. The pump 10 is arranged to operate in parallel with blood flow passing through left ventricle 12. This is effected by inserting an inlet cannula 13 into left ventricle 12 and directing blood flow through the inlet cannula into an inlet of blood pump 10. Blood pump 10, in operational mode, pumps the blood thus received into aorta 14 via outlet cannula 15, as illustrated in FIG. 1.

The blood pump 10 can take a number of forms and rely on a number of different pumping and drive technologies. Broadly, the pump technology can be based on axial or centrifugal rotary pump arrangements or on positive displacement technologies.

In particular, although not limiting forms, preferred pumping technologies for the control system to be described below include rotary pump technologies which rely on an impeller supported for rotation within a casing and which causes blood to be urged between an inlet and outlet of the casing as the impeller rotates therein. In more particular preferred forms a centrifugal form of pump can be utilised with the control system with the characteristics of the pump tailored to compliment or otherwise work particularly advantageously with the control system according to various embodiments of the present invention.

Typically the pump 10 is driven by an electrical power source, in this instance a battery pack 16 mounted externally of the body. Electrical power from the battery pack 16 is controlled by a controller unit 17, also mounted externally of the body. In addition to communicating electrical power to the pump 10 the controller 17 can also communicate with an external programming source, in this case a personal computer 18 for the purposes of initial setup and ongoing periodic monitoring and recalibration of the pump and controller as customised for a specific patient.

Embodiments of a control system suited for use, although not exclusively, with the controller 17 of the arrangement described above and with reference to FIG. 1 will now be described.

Definitions

In the description which follows, the following definitions of various terms as referenced therein are to be utilised:
"non-invasive" is applied to the derivation of various physiological parameters of body 11 (including blood flow rates and the like) by means which do not require sensors to be placed (invasively) within the body.
"IRBP"—implantable rotary blood pump.
"LVAD"—left ventricular assist device.
"LVP"—left ventricular pressure.
"RMS" or "rms"—route mean square.
"V"—volts applied to pump motor.
"I"—current consumed by pump motor.
"SVR"—Systemic Vascular Resistance
"VR"—Venous Resistance
"H"—pump head pressure.
"N"—pump impeller rotation speed.
"Q"—flow rate of blood through pump.
"P" or "PWR"—pump power consumption.
"$\omega$"—angular velocity of impeller.
"t"—time.
Pumping States
"TVC"—total ventricular collapse.
"PR"—pump regurgitation.
"PVC"—partial ventricular collapse.
"AC"—aortic valve closed.
"VE"—ventricle ejecting

First Embodiment

With initial reference to FIGS. 1-4 a first preferred embodiment of a control algorithm and control system is described below and by way of example.

In this embodiment the aim is to provide a pump controller which utilises a control algorithm which takes as its two primary inputs for decision making firstly an indication of the degree of movement of body 11 per unit time as a coarse measure of exertion and hence pumping load required of the heart and particularly left ventricle 12 and secondly an indication of heart rate derived, in this instance, non-invasively by monitoring of electrical parameters driving pump 10.

The system described with reference to FIGS. 1-4 exhibits the following characteristics:
1. Allowing motor speed to vary and deriving control information from those time varying signals; and
2. Concept of using control of power input or speed to the motor/pump.

Figure 2:
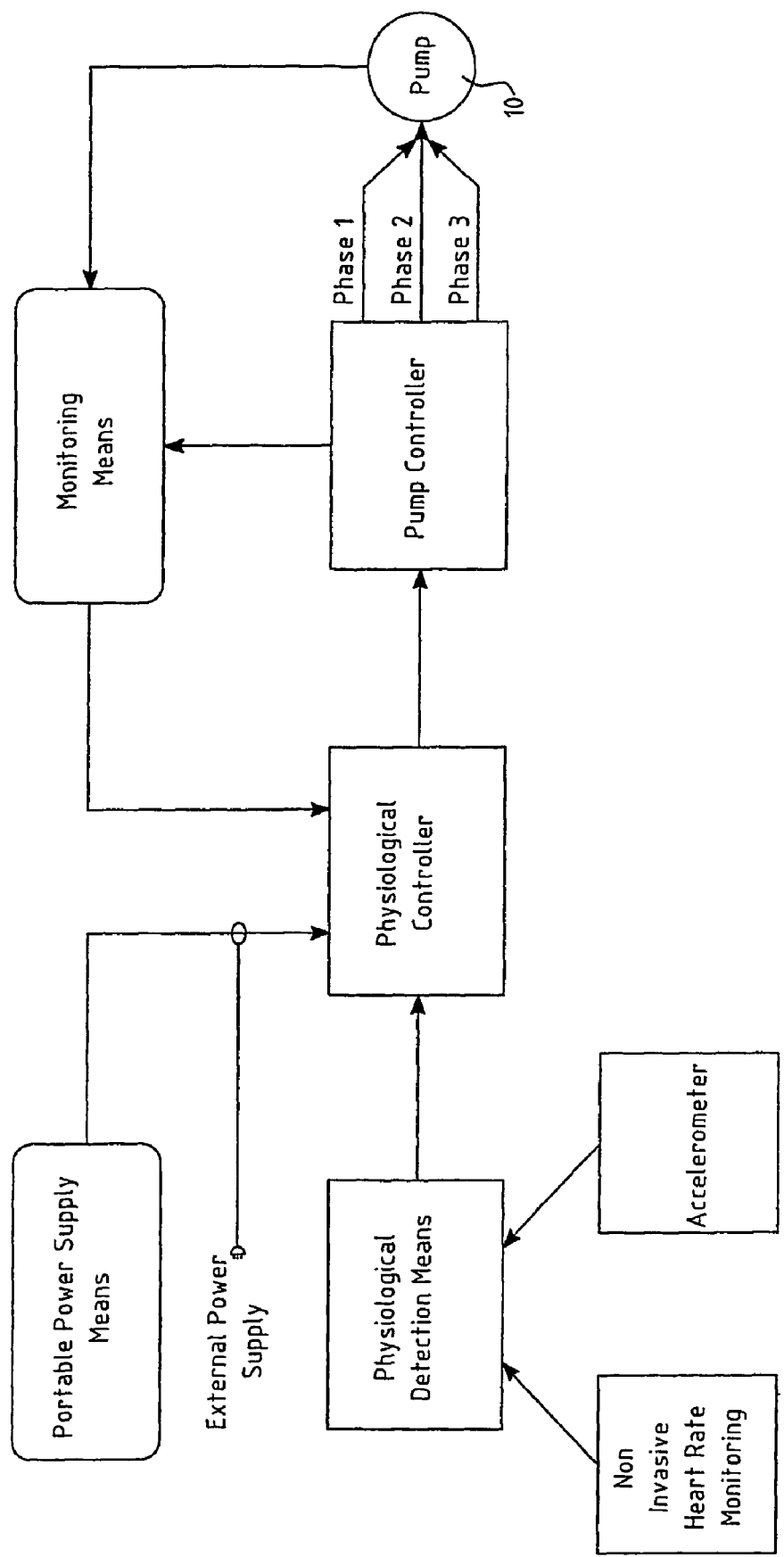
FIG. 2 is a block diagram of a physiological demand responsive of control system applicable to the system of FIG. 1 in accordance with a first preferred embodiment of the present invention.
Figure 3:
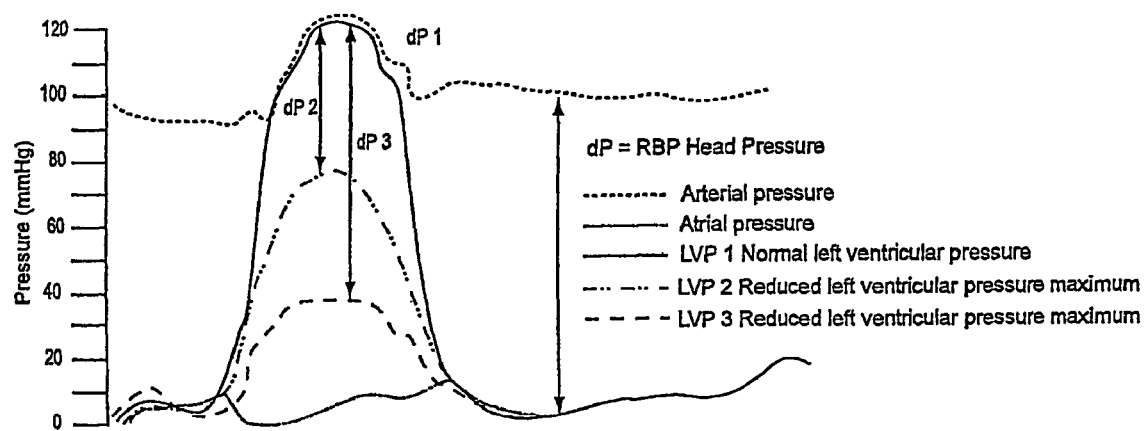
FIG. 3 illustrates graphically the behaviour of the control system of FIG. 2 under specified physiological conditions.

The block diagram shown in FIG. 2 shows the signals that are derived (non-invasively) from pump motor power and speed. To detect these conditions the strategy is to measure speed instantaneously every revolution of the impeller as a digital signal from the motor commutation electronics. The haemo-dynamic controller electronics measure the frequency of this signal which is proportional to impeller speed. Using speed is an advantage since it is a digital signal, which in practice has been found to be an inherently less electrically noisy signal than that derived from measuring motor current or power. Both instantaneous speed and root mean square (rms) of speed are calculated. Also instantaneous pump input power and rms of pump input power are calculated.

Many researchers only discuss constant speed or speed set point. However the present control strategy allows impeller speed and pump input power to be freely modulated by ventricular contractions and uses the resulting dynamic information as feedback to the control system. The characteristics of centrifugal IRBPs mean that impeller speed is more sensitive to hydraulic load variations than for axial IRBPs. Furthermore, allowing impeller speed to vary in magnetically suspended IRBPs may affect suspension control. A preferred pump uses a hydro dynamically suspended impeller and therefore suspension controls are not needed.

Calculation of Instantaneous Impeller Speed N(t) and rms of Impeller Speed Nrms(t)

Each pulse from the commutation controller represents $\frac{1}{6}^{th}$ of a rotation of the impeller and is time stamped relative to a reference time base. Therefore the angular velocity ω of the impeller for each 60° of rotation is described by equation 1.

$$\omega(T) = \frac{2\Pi}{6[(Tn+1) - Tn]} \quad \text{equation 1}$$

where Tn+1−Tn is the time difference between pulses (interrupts) in seconds. ω(t) is converted to speed N(t) in rpm by multiplying by 60/2Π as in equation 2

$$N(t) = \frac{60\varpi(t)}{2\pi} \quad \text{equation 2}$$

Rms speed is calculated in equation 3 from a moving window of samples of N(t), the sample rate dependent on impeller speed. Each instantaneous speed sample is time stamped at $t_1$ to $t_n$.

$$Nrms(t) = \sqrt{\frac{\sum_0^n [N(t)]^2}{n}} \quad \text{equation 3}$$

Calculation of Instantaneous and rms Electrical Input Power Pin(t).

Calculation of pump electrical power is a direct way to monitor the power consumption of the pump. Since the pump power and speed is modulated by the heart which is an asymmetrical modulation (due to the ejection fraction not being 50% rms) calculation of both instantaneous power and speed is implemented. Power is calculated using equation 4.

$$Pin(t) = Vm(t) \cdot Im(t) \quad \text{equation 4}$$

Where Vm(t) and Im(t) are the "instantaneous" motor coil voltage and summed phase current respectively, sampled. A moving window of samples of Pin(t) is used to calculate $P_{rms}(t)$ using equation 5.

$$P_{rms}(t) = \sqrt{\frac{\sum_0^n [Pin(t)]^2}{n}} \quad \text{equation 5}$$

Second Embodiment

Figure 5:
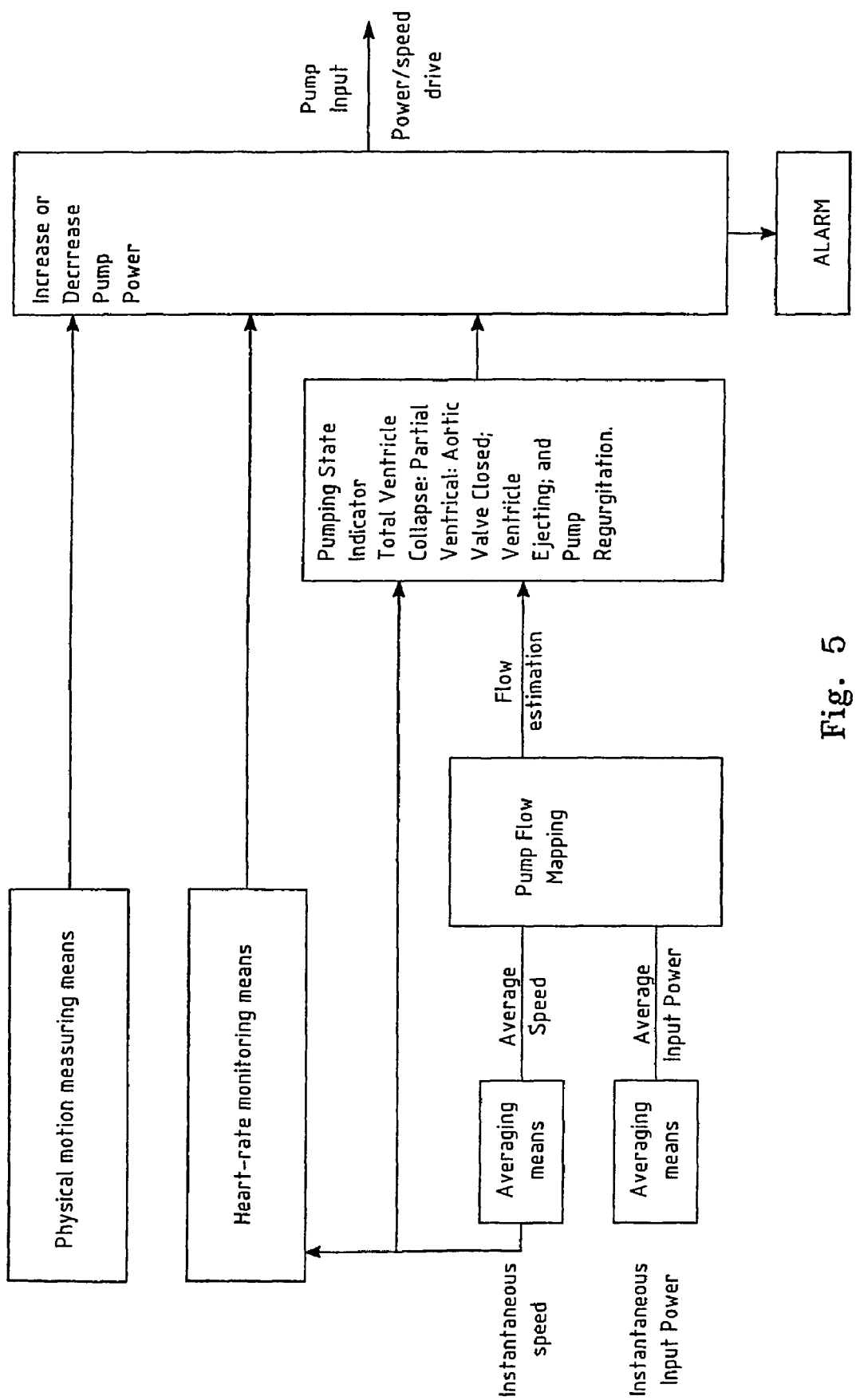
FIG. 5 is a block diagram of a control system in accordance with a second preferred embodiment of the present invention.
Figure 7:
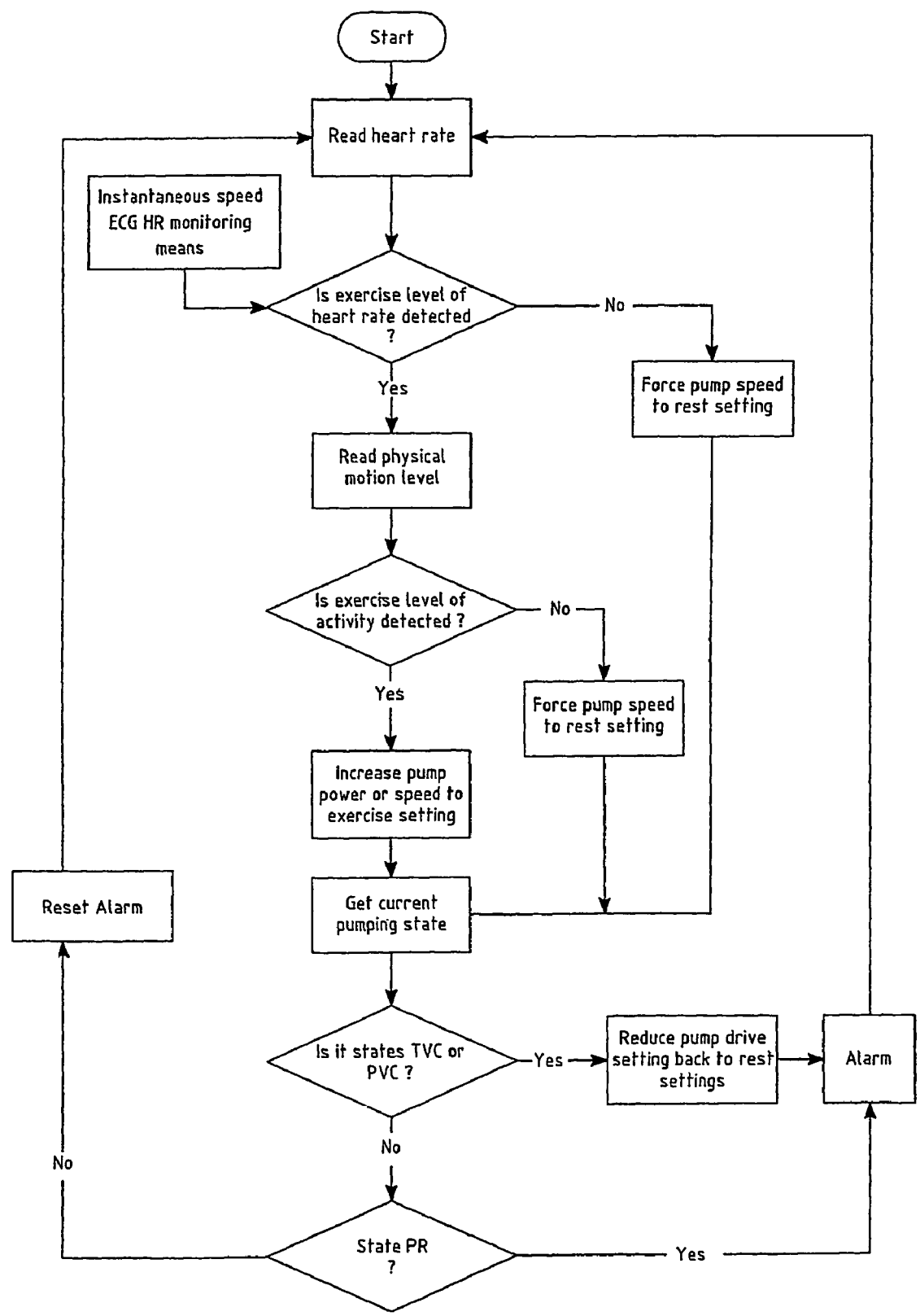
FIG. 7 is a flowchart for determining pump drive set point for the arrangement of the second embodiment.

With reference to FIGS. 5 to 7 inclusive there will now be described a control system in accordance with a second preferred embodiment:

In relation to this second embodiment the control strategy is similar to that described with respect to the first embodiment but, in addition, includes as a further control input derived from non-invasively determined parameters the "pumping state" of pump 10. This feature provides a safety-override mechanism as illustrated in the flowchart of FIG. 7 thereby to ensure that the basic control strategy described with reference to the first embodiment is less likely to put the patient at risk. Initially in the description which follows invasively derived parameters are discussed showing how the various pumping states have been defined and come to be identified. A method of non-invasively deriving the same parameters and pumping state determinations is then described with both forms of derivation being summarised in table 1.

Figure 4:
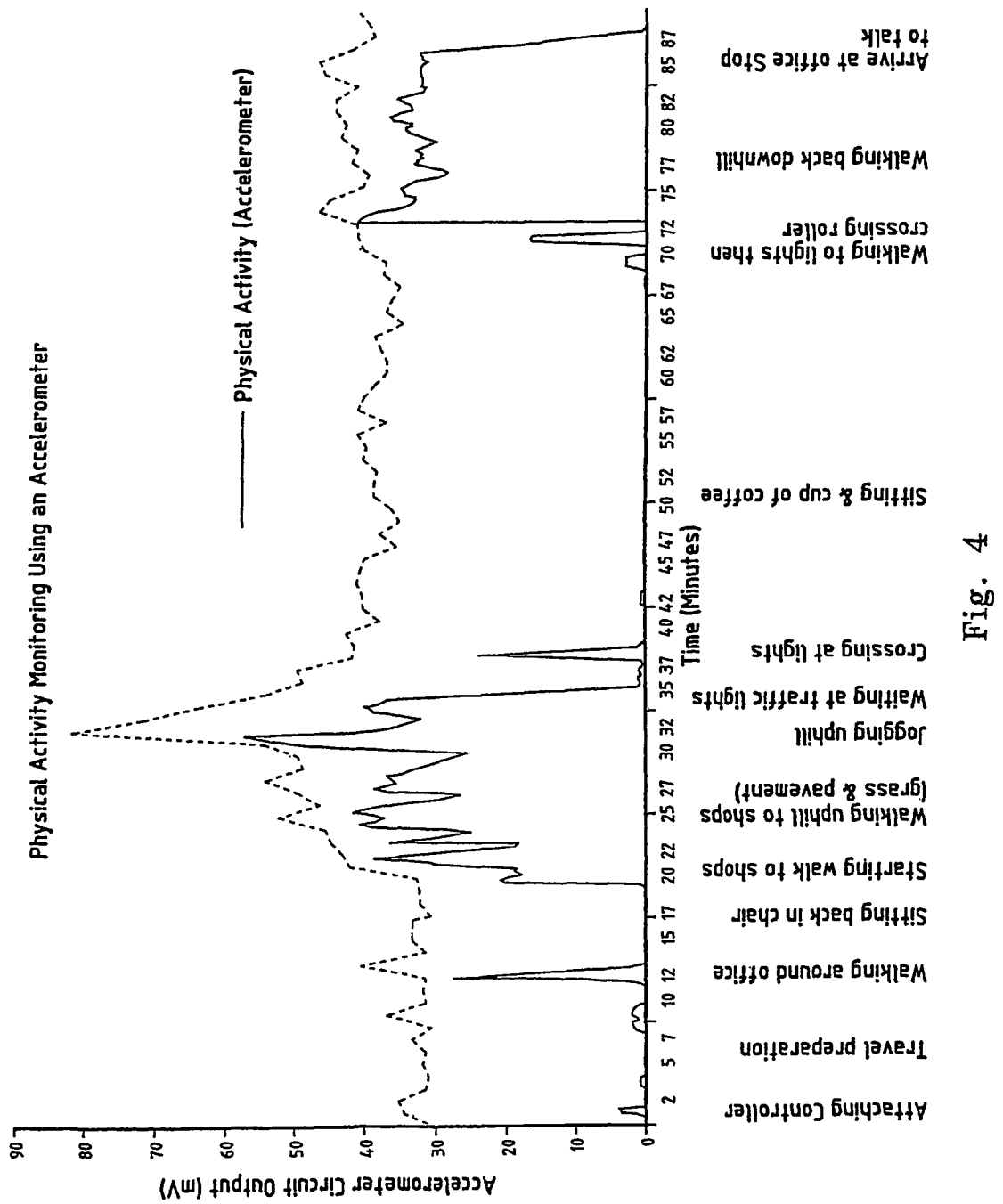
FIG. 4 is a graph of accelerometer behaviour utilised as a basis for an input to the control algorithm of the first preferred embodiment.

With reference to FIG. 4 experimental data suggests that there is a correlation between heart rate and accelerometer output where at least a single axis accelerometer is attached to a patient and used as a measure of physical activity of the patient. This observation is used for the control algorithm now to be described.

FIG. 5 is a block diagram of the control arrangement wherein, in addition to the input variables described with reference to example 1 there is a "physical motion" input which can be derived from an accelerometer associated with a patient. In the simplest form the accelerometer can be a single axis accelerometer. In alternative forms multiple axes of accelerometer sensing can be utilised.

Detection of Physiologically Significant Pumping States

Physiologically critical pumping state detection methods are used based on the non-invasive system observers pump speed and electrical input power. Activity level is detected using heart rate (detected from pump impeller instantaneous speed) and motion by using an accelerometer although other measuring devices may be used without departing from the scope of the present invention. These non-invasive observers are utilised as inputs to a control algorithm for a rotary blood pump to seek to ensure that pump output is better adapted to patient rest and exercise states.

Identifying Pumping States

Methods were developed to detect pumping states based on instantaneous measured pump power and speed. The methods developed allow impeller speed and pump input power to be freely modulated by ventricular contractions. This dynamic information is utilised as feedback to the control system. Data from in-vitro and in-vivo experiments shows that states TVC (total ventricular collapse) and PR (pump regurgitation) produce low flow through the pump. State TVC produces non-pulsatile low flow while state PR produces pulsatile low flow less than 1 L/min. States PVC (Partial Ventricular Collapse), AC (Aortic valve Closed) and VE (Ventricle Ejecting) produce normal pump flows greater than 1 L/min. States PVC and PR can be differentiated from state AC since flow pulsatility is more evident. State PVC can be differentiated from state VE since the dynamic flow symmetry is different from all other states. The dynamic nature of the flow is reflected by pump speed and power. Instantaneous measured pump speed is used to indicate flow dynamics.

Detecting of State TVC, Ventricle Totally Collapsed Occluding the Inlet Cannula.

Examining the in-vitro and in-vivo data it has been found that state TVC can be consistently detected by fall in pump flow to near 0 L/min accompanied by a reduction of flow pulsatility. It has been observed Flow waveform symmetry may not be relevant for detection of this state.

Detecting State PVC, Ventricle not Ejecting and Beginning to Collapse onto the Cannula The state PVC is indicated by a variation in symmetry of the instantaneous speed waveform given a level of pulsatility. Given that normal flow rates can still be observed during this state and that flow pulsatility is large, the only parameter distinguishing this state from the VE state is the flow symmetry.

State AC Ventricle not Ejecting and Positive Pump Flow.

By analysing the cardiac cycle with the pump it has been was found that there may be a portion of state AC where the aortic valve remains closed, whilst however the pump flow is still pulsatile. Assistance beyond this point causes pump flow pulsatility to reduce. At high perfusion demands, as in exercise, the failed ventricle may be supplemented to such an extent that the flow through the pump is pulseless. Theoretically if no left ventricle contraction occurs then implantable rotary blood plump flow will be non pulsatile. Contraction of the left ventricle with the pump connected means that pump head is proportional to the difference between the aortic pressure and the left ventricular pressure (LVP). If the pump power is increased beyond the point that the left ventricle is doing no work (the aortic valve no longer opens) maximum LVP begins to decrease. This means that minimum instantaneous pump differential pressure will begin to rise relative to the RMS of the pump differential pressure over the cardiac cycle. If the ventricle is weakened through heart failure this will occur at relatively lower pump speeds and the mitral valve will still continue to open and LVP maximum will decrease towards zero with increasing speeds. During this interval the mitral valve will open and close. Steady flow occurs when there is no pulsatility in the speed signal and the mitral valve never closes. The target speed at which this occurs will increase with SVR or VR and cardiac contractility. Continuing to increase the pump power will cause the transition from pulsatile to non pulsatile flow. This means detection of the state VE and state AC can only be achieved dynamically by considering the maximum instantaneous speed Nmax(t) and the rms of instantaneous speed Nrms(t) for the nth and (n−1)th cardiac cycle. A significant change occurs only if there is a change in average pump speed set point, after load or pre load. A method of detecting the AC state without relying on transitions has been chosen which uses peak to peak flow rate given that pump flow is greater than 1 L/min.

Detecting State VE, Ventricle Ejecting with Positive Pump Flow

State VE may be identified non invasively by pump flow rate being larger than 1 L/min and peak to peak instantaneous voltage (flow) being greater than a threshold value and the flow symmetry being greater than that for the PVC state.

Detecting State Pr: The Point at which Pump Flow Rate is Less than Zero

The PR state may be indicated when the pump flow falls below the lower flow limits Qmin which is set to be 1 L/min. This level of Qmin is set at 1 L/min although not "0 L/min" may be was considered a safe limit to be classed as retrograde flow.

Pumping State Detection Using Non-Invasive Pump Parameters

By analysing pump parameters deriving from invasive-derived parameters it is postulated that flow, flow amplitude and waveform symmetry appear to be good indicators of pumping state using only non-invasively-derived pump parameters. These variables can be detected non-invasively using estimated pump flow (Qest,), peak to peak instantaneous speed Npp(n) and symmetry Nsym(n). Table 1 shows the relationship of physiological parameters to non-invasive pump parameters for each of the physiologically identified pumping states which have been taken from in-vitro and in-vivo data sets (n=3).

TABLE 1

A summary of physiological (invasive) and pump (non-invasive) parameters used as the criteria to identify pumping states.
Identifying Parameters

| State | Invasion (Physiological) | | | | Non-invasive via pump (from speed and power) | | |
| --- | --- | --- | --- | --- | --- | --- | --- |
| | AoP mmHg | Pulse Press. (mmHg) | LVP max (mmHg) | Qav (L/min) | $Q_{estRMS}(t)$ (L/min) | $Q_{sym}(n)$ | Npp(n) (rpm) |
| TVC | <40 | <10 | <40 | <1 | <1 | — | <30 |
| PVC | 60-180 | >10 | 60-180 | <1 | >1 | <0.4 | >30 |
| AC | 60-180 | <10 | <AoP | <1 | >1 | — | <30 |
| VE | 60-180 | >10 | >AoP | >1 | >1 | >0.4 | >30 |
| PR | 60-180 | >10 | >AoP | >1 | <1 | >0.4 | >30 |

Estimated pump flow $Q_{est}$ is derived from $N_{rms}(t)$ and $PWR_{rms}(t)$. The RMS of instantaneous pump speed $N_{rms}(t)$ and power $PWR_{rms}(t)$ are derived from instantaneous speed N(t) and power PWR(t). The haemo-dynamic controller electronics measure the frequency of the speed signal, which is proportional to impeller speed. Using speed rather than power as an observer for dynamic changes is an advantage since it is a digital signal, substantially free from electrical noise which may contribute to error.

Detecting Low Flow

Equation 6 is used to model low and normal flow rate through the pump based on RMS impeller speed and electrical input power.

$$Q_{est} \alpha K + \text{speed} + \text{Pwr} + (\text{Pwr})^2 + (\text{Pwr})^3 \qquad \text{equation 6}$$

A flow Index, $Q_p$Index, shown in equation 7 is developed to distinguish between low flow rates and normal flow rates by incorporating $Q_{est}$. If $Q_p$Index>50 this corresponds in this example to a flow rate greater than 1 L/min. A QpIndex <50 means that flow is less than 1 L/min or "low flow"

$$Q_p\text{Index} = 50 \cdot Q_{est} \qquad \text{equation 7}$$

Both the TVC and the PR pumping states defined and discussed produce low pump flow rates. States PVC, AC and VE produce "normal" flow rates where the circulation is not compromised.

Detecting Pulsatile Flow

States TVC and AC produce near non pulsatile pump flow. The difference between these states is that state AC occurs when the circulation is supported and state TVC when it is not. These states can be differentiated by comparing $Q_{est}$Index. States PVC, VE and PR produces pulsatile flow. States PVC and VE produce flow which supports the circulation whereas state PR compromises the circulation due to back flow through the pump. It has been shown that instantaneous speed amplitude is proportional to pump flow amplitude. The flow pulsatility index $Q_{p\cdot p}$ Index (equation 9) is developed based on instantaneous speed amplitude $N_{p\cdot p}(n)$ (equation 8) which is equal to the difference between the maximum and the minimum instantaneous impeller speed $N_{max}(n)$ and $N_{min}(n)$ for the $n^{th}$ cardiac cycle. The index outputs a value greater than 50 for pulsatile flow and less than 50 for non pulsatile flow.

$$N_{p-p}(n) = N_{max}(n) - N_{min}(n) \qquad \text{equation 8}$$

$$Q_{p-p}\text{Index} = 50 \cdot \frac{Q_{p-p}\text{min}}{N_{p-p}(n)} \qquad \text{equation 9}$$

Detecting Variations in Flow Symmetry

The in-vitro and in-vivo data show that instantaneous speed reflects the inverse symmetry of pump flow whilst current reflects the same symmetry, although speed exhibits less electrical noise. Thus it is postulated that the symmetry of flow can be estimated by using the inverted symmetry of instantaneous speed.

States PVC and VE both produce flow rates which support the circulation and a degree of pulsatility. Differentiating between states can be achieved by considering the symmetry of the flow wave form which is reflected in instantaneous speed. The symmetry of flow rate is an inversion of the instantaneous speed signal. The flow symmetry index $Q_{sym}$Index (equation 11) is developed by using the inverted speed waveform symmetry defined by equation 10 with the symmetry threshold $Q_{sym}$MAX set at 0. The index is set so that if the flow symmetry falls below 0.3 (speed symmetry rises above 0.7) its output is less than 50.

$$N_{sym} = \frac{(N_{rms}(n) - N_{min}(n))}{N_{p-p}(n)} \qquad \text{equation 10}$$

$$Q_{sym}\text{Index} = 50 \frac{Q_{sym}\text{MAX}}{N_{sym}}. \qquad \text{equation 11}$$

Determining the Current Pumping State from Non-Invasive Indicators

The block diagram shown in FIG. 5 shows the module that combines the detection methods discussed above derived from instantaneous power and speed. The current state is determined by the logic table shown in FIG. 10 where flow, flow pulsatility and symmetry are used to decide the present pumping state.

Detection of Heart Rate Using Pump Speed

While pulsatile flow is detected, the heart rate is calculated by using the array of speed samples. For the entire speed array $N[t_1-t_n]$ of samples the frequency of speed is calculated by using the derivative of speed and detecting the time of the speed maxima and minima. The derivative of speed is defined in equation 12.

$$\frac{dN(t_n)}{dt} = \frac{N(t_n) - N(t_{n-1})}{\Delta t} \qquad \text{equation 12}$$

HR is then calculated by time stamping the maxima and minima of the speed signal given by HRa and HRb in is equations 13 and 14. The average is then computed and used as HR using equation 15. Speed maxima are detected by $dN(t_n)/dt$ changing from a positive to a negative value. Speed minima are detected by $dN(t_n)/dt$ changing from a negative to a positive value. $T_{max(n)}, t_{max(n-1)}, t_{min(n)}, t_{min(n-1)}$ are the time stamps for the maximum and minimum values of instantaneous speed.

$$HRa = \frac{60}{[t\max(n) - t\max(n-1)]} \qquad \text{equation 13}$$

$$HRb = \frac{60}{[t\min(n) - t\min(n-1)]} \qquad \text{equation 14}$$

$$HR = \frac{HRa + HRb}{2} \qquad \text{equation 15}$$

Detection of Physical Motion

An accelerometer is mounted in the controller electronics and used to detect physical motion. The accelerometer output is amplified by a differential amplifier and integrated to provide a signal level indicating continuous physical motion.

A preferred embodiment of the present invention of the physiological demand responsive controller is suited for used with implantable third generation LVASs. Also, a further embodiment of the present invention is designed to cooperate with a Ventrassist™ left ventricle assist system (LVAS).

One of the preferred embodiments may automatically adjust the pumping speed of an implanted third generation blood pump to an optimal level for the varying physiological needs of the implanted patient. The preferred embodiment may achieve this by periodically iteratively changing the speed setpoint of the pump. When the control system detects increased physiological demand by the patient (e.g. by physical exertion) the controller will increase the pumping speed accordingly. The pumping state of the patient's heart and physiological demand of the patient will be computed by the control system in real time as functions of the pump's motor power and speed setpoint of the pump. Additionally, the physiological demand of the patient may also be detected by the use of a three axis accelerometer.

This accelerometer may be able to detect the instantaneous motion of the patient. Preferably, this instantaneous motion may also be indicative of the relative motion of the patient. The output of the accelerometer may preferably be directed into a conditioning circuit to digitise and filter the output signal of said accelerometer. This signal will then be passed from the conditioning circuit to a computational module which derives a physiological demand state (eg. resting, sleeping, exercising, or patient collapse) as a numerically represented version of the state (eg. 1=resting; 2=sleeping etc). The numerically represented version of the physiological demand state may then be inputted into the control system for a pumping device or medical device. The pumping speed of the implantable blood pump may then be altered in respect of the predetermined range for physiological demand for a particular patient.

Preferably, the predetermined ranges of pumping speeds will be set by a specialist doctor at the time of implantation of the blood pump. Additionally, it may be preferable to allow doctors to amend the predetermined range as they see fit.

Figure 9:
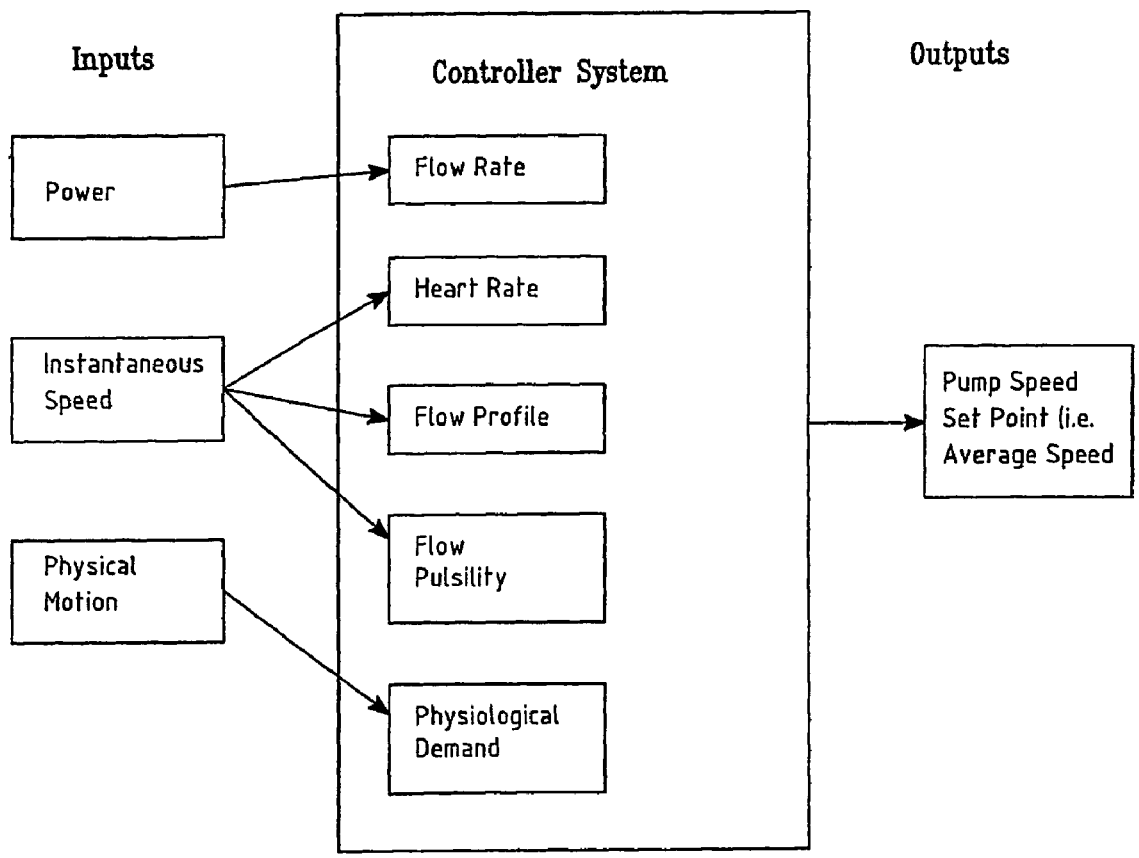
FIG. 9 is a diagram of a preferred embodiment of the present invention wherein said diagram shows preferred inputs and outputs.

Preferably in an embodiment of the present invention the control system may include a specialised algorithm. This algorithm may include a mathematical model of ideal pumping speed of an implantable blood pump for suitable physiological conditions of the patient. This algorithm may receive input or data included within three broad areas of data. These areas of data may include pump power, instantaneous pump speed and physical motion. The algorithm within the controller system (see FIG. 9) may use these areas of data to predict certain patient data. This patient data may include blood flow rate, heart rate, flow profile, pulsatility and physiological demand. The algorithm will then output the preferred pump speed and the remainder of the controller system will use this information to set a speed setpoint for the blood pump.

Preferably, an embodiment of the present invention will be such that iterative changes will be able to be made in timely manner.

In a further embodiment of the present invention, a preferred physiological demand responsive controller system may be adapted for use with a radial off flow type centrifugal blood pump.

The above describes only some embodiments of the present invention and modifications, obvious to those skilled in the art, can be made thereto without departing from the scope and spirit of the present invention.

Figure 8:
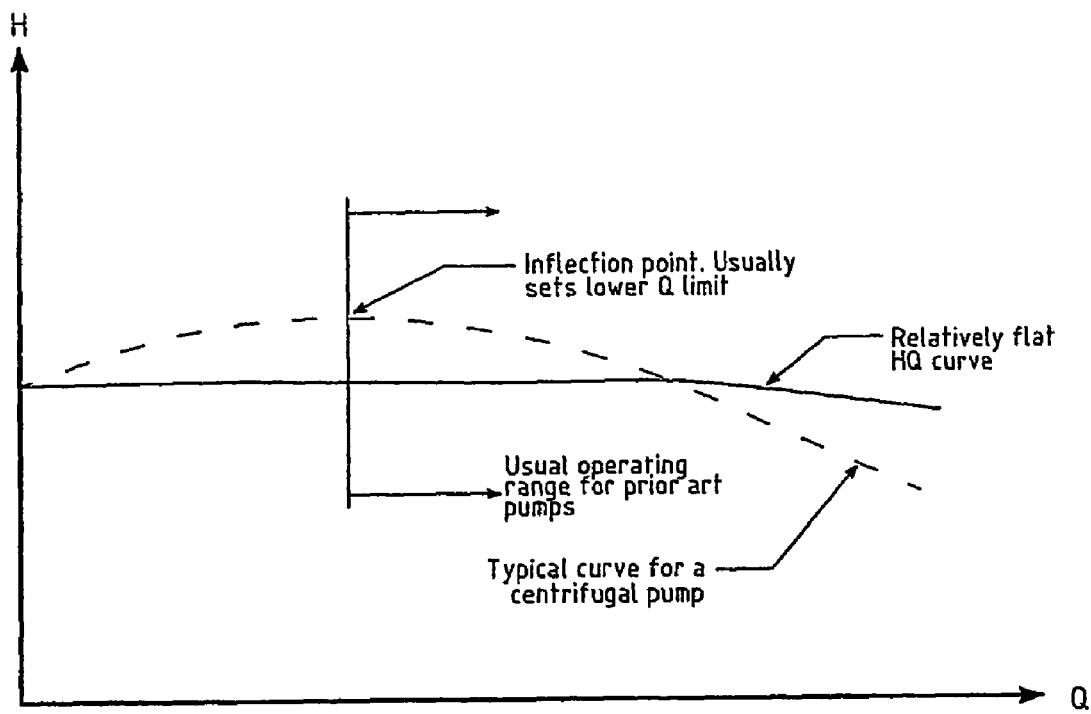
FIG. 8 illustrates graphically an HQ curve for a preferred pump type particularly suited for use with the control system of FIG. 2 or FIG. 5.

The system is particularly suited for use with pumps which exhibit a relatively flat HQ curve as described with reference to FIG. 8. In particular, but not exclusively, pumps of the radial off flow type as, for example, described in International Patent Application PCT/AU98/00725 can exhibit this relatively flat characteristic. The description of PCT/AU98/00725 is incorporated herein by cross-reference.

The invention claimed is:

1. A demand responsive physiological control system for use with a blood pump;
    said system including a pump controller which is capable of controlling pump speed;
    said system further including a physiological controller adapted to analyze input data indicative of at least one physiological state of a user of said pump, wherein said physiological controller determines appropriate pumping speed and sends a speed control signal to said pump controller to adjust pump speed; and
    said system further including a physiological state detector which provides said input data indicative of at least one physiological state of the user to said physiological controller;
    wherein said input data indicative of at least one physiological state of the user is derived from signals received from a non-invasive sensor adapted for detecting physical motion of the user.

2. The system as in claim 1, wherein said system includes a pump monitor that detects information relating to current of the pump and delivers this information to said physiological controller.

3. The system as in claim 2 wherein the pump monitor detects an pump impeller speed and uses this information to derive a heart rate.

4. The system as in claim 3 wherein said physiological controller uses said information received from the pump monitor to derive mathematically an appropriate pump speed.

5. The system as in claim 4 wherein the physiological controller assesses flow dynamics and an average flow estimate developed from speed and input power supplied to the pump by the pump controller.

6. The system as in claim 4 wherein the physiological controller mathematically determines a pumping state and if a deleterious state is determined the speed control signal is changed accordingly.

7. The system as in claim 6 wherein the physiological detector includes a means of detecting and quantifying a heart rate of the user, when in use.

8. The system as in claim 1 wherein the physiological detector includes a means of non-invasively detecting and quantifying a heart rate of the user.

9. The system as in claim 8 wherein, the physiological controller can determine a heart rate of the user using power input to the pump.

10. The system as in claim 1 wherein the pump is internally implantable within the user.

11. The system as in claim 10 wherein the pump is a ventricle assist device.

12. The system as in claim 1, wherein said physiological controller is adapted for communicating with a computer for manual manipulation of a predefined range of physiological states which are receivable as input to the physiological controller.

13. The system as in claim 1, wherein the non-invasive sensor is mounted in the pump.

14. A demand responsive physiological control system for use with a blood pump; said system including a pump controller which is capable of controlling pump speed; said system further including a physiological controller adapted to analyze input data indicative of at least one physiological state of a user of said pump, wherein said physiological controller determines appropriate pumping speed and sends a speed control signal to said pump controller to adjust pump speed; and said system further including a physiological state detector which provides said input data indicative of at least one physiological state of the user to said physiological controller;
    wherein the physiological state detector includes an accelerometer to sense motion of the user, when in use, the accelerometer sensing motion in three orthogonal axes;
    wherein said system includes a pump monitor that detects information relating to voltage and current of the pump and delivers this information to said physiological controller;
    wherein the pump monitor detects a pump impeller speed of the pump through non-invasive measurements;
    wherein said physiological controller uses said information received from the pump monitor to derive mathematically an appropriate pump speed;
    wherein the physiological controller assesses flow dynamics and an average flow estimate developed from speed and input power supplied to the pump by the pump controller;
    wherein the physiological controller mathematically determines a pumping state and if a deleterious state is determined the speed control signal is changed accordingly;

wherein the physiological detector includes a means of detecting and quantifying a heart rate of the user, when in use;

wherein the physiological detector includes a means of non-invasively detecting and quantifying a heart rate of the user, in use;

wherein, the physiological controller can determine a heart rate of the user using power input to the pump;

wherein the pump is internally implantable within the user;

wherein the physiological controller is capable of manual manipulation by the user.

15. The system as in claim 14 wherein the manual manipulation is within adjustable predefined limits.

16. The system as in claim 15 wherein the physiological controller is adapted for communication with a computer and wherein the physiological controller, is adapted for manipulation by a software user interface.

17. The system as in claim 16 wherein the physiological controller includes an alarm.

18. A demand responsive physiological control system for use with a blood pump, comprising:

a sensor for detecting physical motion of a user of the pump; and a controller capable of controlling pump speed including adjusting pump speed based on a detected physiological state, wherein the physiological state is detected from both data received from the sensor and a detected heart rate of the user;

wherein both the heart rate and physical motion of the user are detected non-invasively.

19. The control system as in claim 18, wherein the sensor is a non-invasive sensor whereby the sensor is not implanted in the body separate from the controller or pump.

20. The control system as in claim 18, wherein the controller is capable of detecting a physiological state including motion of the user relative to his or her surroundings using the detected heart rate and data received from the sensor.

21. The control system as in claim 18, wherein the heart rate is computed non-invasively by using the instantaneous pump speed.

22. The control system as in claim 18, wherein the sensor is mounted in the pump or the controller.

* * * * *